United States Patent
Frisken et al.

(10) Patent No.: US 12,082,883 B2
(45) Date of Patent: Sep. 10, 2024

(54) ENHANCED PLANNING AND VISUALIZATION WITH CURVED INSTRUMENT PATHWAY AND ITS CURVED INSTRUMENT

(71) Applicants: Canon U.S.A., Inc., Melville, NY (US); The Brigham and Women's Hospital Incorporated, Boston, MA (US); Sarah Frisken, Cambridge, MA (US); Clement Mirabel, Brookline, MA (US); Parikshit Juvekar, Brookline, MA (US); Takahisa Kato, Brookline, MA (US); Alexandra J. Golby, Jamaica Plain, MA (US); Garth R. Cosgrove, Boston, MA (US); Thomas Noh, Boston, MA (US)

(72) Inventors: Sarah Frisken, Cambridge, MA (US); Clement Mirabel, Brookline, MA (US); Parikshit Juvekar, Brookline, MA (US); Takahisa Kato, Brookline, MA (US); Alexandra J. Golby, Jamaica Plain, MA (US); Garth R. Cosgrove, Boston, MA (US); Thomas Noh, Boston, MA (US)

(73) Assignees: Canon U.S.A., Inc., Melville, NY (US); The Brigham and Women's Hospital Incorporated, Boston, MA (US)

( * ) Notice: Subject to any disclaimer, the term of this patent is extended or adjusted under 35 U.S.C. 154(b) by 55 days.

(21) Appl. No.: 17/791,168

(22) PCT Filed: Jan. 8, 2021

(86) PCT No.: PCT/US2021/012715
§ 371 (c)(1),
(2) Date: Jul. 6, 2022

(87) PCT Pub. No.: WO2021/142272
PCT Pub. Date: Jul. 15, 2021

(65) Prior Publication Data
US 2023/0044706 A1    Feb. 9, 2023

Related U.S. Application Data

(60) Provisional application No. 62/959,095, filed on Jan. 9, 2020.

(51) Int. Cl.
*A61B 34/10*    (2016.01)
*A61B 34/20*    (2016.01)

(52) U.S. Cl.
CPC .............. *A61B 34/10* (2016.02); *A61B 34/20* (2016.02); *A61B 2034/105* (2016.02); *A61B 2034/107* (2016.02)

(58) Field of Classification Search
None
See application file for complete search history.

(56) References Cited

U.S. PATENT DOCUMENTS

| | | |
|---|---|---|
| 7,167,738 B2 | 1/2007 | Schweikard et al. |
| 7,491,198 B2 | 2/2009 | Kockro |

(Continued)

FOREIGN PATENT DOCUMENTS

| | | |
|---|---|---|
| CN | 110111880 A | 8/2019 |
| EP | 0822785 B1 | 11/2004 |

(Continued)

OTHER PUBLICATIONS

Alterovitz, Ron, Michael Branicky, and Ken Goldberg. "Constant-curvature motion planning under uncertainty with applications in image-guided medical needle steering." (Year: 2008).*

(Continued)

*Primary Examiner* — Ryan M Gray
(74) *Attorney, Agent, or Firm* — Canon U.S.A., Inc., IP Division

(57) ABSTRACT

Exemplary methods and systems that provide a curved path trajectory that can be used with a bendable medical device.

(Continued)

The curved pathway can comprise straight and curved concatenated arc segments. The methods and systems can provide planning, visualizing and treatment of, for example, temporal lobe epilepsy (TLE) using laser interstitial thermal therapy (LITT) or tumors using ablation therapy. With curved pathway, the physician can create plan for intervention to avoid critical structure and to cover more target volume for treatment/diagnosis than straight pathway.

21 Claims, 13 Drawing Sheets

(56) References Cited

U.S. PATENT DOCUMENTS

| | | | |
|---|---|---|---|
| 8,065,011 | B2 | 11/2011 | Echauz et al. |
| 8,340,743 | B2 | 12/2012 | Jenkins et al. |
| 8,417,491 | B2 | 4/2013 | Trovato et al. |
| 8,634,897 | B2 | 1/2014 | Simon et al. |
| 9,008,414 | B2 | 4/2015 | Merkl et al. |
| 9,278,203 | B2 | 3/2016 | Averbuch |
| 9,387,047 | B2 | 7/2016 | Trovato |
| 9,600,138 | B2 | 3/2017 | Thomas et al. |
| 9,700,342 | B2 | 7/2017 | Andrews et al. |
| 9,734,632 | B2 | 8/2017 | Thomas et al. |
| 9,818,231 | B2 | 11/2017 | Coffey et al. |
| 9,911,187 | B2 | 3/2018 | Steinle et al. |
| 10,398,387 | B2 | 9/2019 | Merkl et al. |
| 10,433,763 | B2 | 10/2019 | Piron et al. |
| 10,687,694 | B2 | 6/2020 | Tanaka et al. |
| 11,007,641 | B2 | 5/2021 | Takagi et al. |
| 11,051,892 | B2 | 7/2021 | Hata et al. |
| 11,096,552 | B2 | 8/2021 | Hata et al. |
| 11,103,992 | B2 | 8/2021 | Tanaka et al. |
| 11,278,366 | B2 * | 3/2022 | Kose .......... A61B 34/74 |
| 2007/0142873 | A1 | 6/2007 | Esteller et al. |
| 2008/0160489 | A1 | 7/2008 | Bruijns |
| 2009/0131783 | A1 | 5/2009 | Jenkins et al. |
| 2011/0077508 | A1 | 3/2011 | Simon et al. |
| 2015/0049081 | A1 | 2/2015 | Coffey et al. |
| 2015/0265366 | A1 | 9/2015 | Andrews et al. |
| 2015/0351860 | A1 | 12/2015 | Piron et al. |
| 2016/0070436 | A1 | 3/2016 | Thomas et al. |
| 2017/0252114 | A1 * | 9/2017 | Crawford .......... A61B 17/1757 |
| 2017/0296289 | A1 * | 10/2017 | Andrews .......... A61B 18/24 |
| 2017/0340240 | A1 | 11/2017 | Jacobsen et al. |
| 2017/0348056 | A1 * | 12/2017 | Steinle .......... A61B 34/30 |
| 2018/0217734 | A1 | 8/2018 | Koenig et al. |
| 2018/0296800 | A1 | 10/2018 | Kato et al. |
| 2019/0010546 | A1 | 1/2019 | Hue et al. |
| 2019/0105105 | A1 | 4/2019 | Zagorchev et al. |
| 2019/0105468 | A1 | 4/2019 | Kato et al. |
| 2019/0374746 | A1 | 12/2019 | Konh |
| 2020/0146754 | A1 * | 5/2020 | Row .......... A61B 90/39 |
| 2020/0281676 | A1 * | 9/2020 | Rohs .......... A61B 34/10 |
| 2020/0330159 | A1 | 10/2020 | Zhang et al. |
| 2020/0383670 | A1 | 12/2020 | Okumura et al. |
| 2023/0091099 | A1 * | 3/2023 | Wang .......... A61B 34/20 |

FOREIGN PATENT DOCUMENTS

| | | |
|---|---|---|
| EP | 3035884 A1 | 6/2016 |
| EP | 3200717 B1 | 3/2018 |
| JP | 2003-030624 A | 1/2003 |
| JP | 2008531108 A | 8/2008 |
| JP | 2009-511155 A | 3/2009 |
| JP | 2012-533333 A | 12/2012 |
| JP | 2016-508762 A | 3/2016 |
| WO | 2017/043926 A1 | 3/2017 |

OTHER PUBLICATIONS

Bergeles, Christos, et al. "Concentric tube robot design and optimization based on task and anatomical constraints." IEEE Transactions on Robotics 31.1 (2015): 67-84. (Year: 2015).*

Pinzi, S., et al., "The Adaptive Hermite Fractal Tree (AHFT): a novel surgical 3D path planning approach with curvature and heading constraints," Int J Comput Assist Radiol Surg, Apr. 2019, pp. 659-670, vol. 14, No. 4.

Hong, A., et al., "3D path planning for flexible needle steering in neurosurgery," Int J Med Robot, 2019, pp. e1998, vol. 15, No. 4.

Granna, J., et al., "A 3-D Volume Coverage Path Planning Algorithm With Application to Intracerebral Hemorrhage Evacuation", IEEE Robotics and Automation Letters, Jul. 2016, vol. 1, No. 2, pp. 876-881.

Comber, D.B., et al., "Optimization of Curvilinear Needle Trajectories for Transforaminal Hippocampotomy", Operative Neurosurgery, Feb. 2017, pp. 15-23, vol. 13, No. 1.

Kim, Y., et al., "Toward the Development of a Flexible Mesoscale MRI-compatible Neurosurgical Continuum Robot," IEEE Trans Robot, Dec. 2017, pp. 1386-1397, vol. 33, No. 6.

Webster, R.J., et al., "Design and kinematic modeling of constant curvature continuum robots: A review," International Journal of Robotics Research, 2010, pp. 1661-1683, vol. 29, No. 13.

Wu, C., et al., "What is the Best Target for Ablation of Mesial Temporal Lobe Epilepsy", 2019, pp. 313-315, vol. 19, No. 5.

Wu, C., et al., "Effects of Surgical Targeting in Laser Interstitial Thermal Therapy for Mesial Temporal Lobe Epilepsy: A Multicenter Study of 234 Patients", Epilepsia, 2019, pp. 1171-1183, vol. 60.

Granna, J., et al., "Computer-assisted planning for a concentric tube robotic system in neurosurgery", Int J Comput Assist Radiol Surg, Feb. 2019, pp. 335-344, vol. 14, No. 2.

Zhao, Y.J., et al., "Path Planning to Robot-Assisted Active Flexible Needle using Improved Rapidly-Exploring Random Trees", IEEE Xplore, pp. 380-383.

Pinter, C., et al., "Polymorph segmentation representation for medical image computing", Comput Methods Programs Biomed, Apr. 2019, pp. 19-26, vol. 171.

Gao, Y., et al., "Continuum Robot with Follow-the-Leader Motion for Endoscopic Third Ventriculostomy and Tumor Biopsy", IEEE Trans Biomed Eng., Feb. 2020, pp. 379-390, vol. 67, No. 2.

Daisne, J.F., et al., "Atlas-based automatic segmentation of head and neck organs at risk and nodal target volumes: a clinical validation", Radiation Oncology, 2013, pp. 1-11, vol. 8, No. 154.

Gupta, K., et al., "Robot Assisted MRI-Guided LITT of the Anterior, Lateral, and Medial Temporal Lobe for Temporal Lobe Epilepsy", Front. Neurol., Nov. 27, 2020, vol. 11.

* cited by examiner

ENHANCED PLANNING AND VISUALIZATION WITH CURVED INSTRUMENT PATHWAY AND ITS CURVED INSTRUMENT

CROSS REFERENCE TO RELATED PATENT APPLICATIONS

This application is a National Phase application of International Application No. PCT/US21/1271, filed 8 Jan. 2021, which claims priority from U.S. Provisional Application No. 62/959,095 filed on 9 Jan. 2020 in the United States Patent and Trademark Office, the disclosure of which is incorporated herein in its entirety by reference.

U.S. GOVERNMENT RIGHTS

This invention may have been made in the performance of work under NIH grants P41-EB015898 and Ro1-EB027134. The government may have rights in this invention.

FIELD OF THE DISCLOSURE

The disclosure of this application relates generally to medical system with software and devices and in particular to computer aided system with a curved device applicable to guide interventional tools and instruments, such as catheters and ablation probes.

BACKGROUND INFORMATION

Minimally invasive intervention is gaining wide adoption in many medical areas. For example, in neurosurgical procedures, Laser Interstitial Thermal Therapy (LITT) has been associated with cost-appropriate improvement in survival, the ability to treat deep and otherwise surgically inaccessible lesions in brain surgery. In addition, since LITT bypasses the blood brain barrier, it is showing promise for targeted drug delivery. Specifically, in Epilepsy, LITT is now a first-line surgical option for pediatric hypothalamic hamartoma, and is accepted as an upfront surgical option to medial epilepsy.

LITT is a minimally invasive therapeutic technique including tumor ablation, treatment of radiation necrosis and epilepsy. LITT uses a catheter with a diode laser tip that is stereotactically placed inside the brain through a 2-3 mm diameter cannula. The cannula passes through the skull and the brain parenchyma to the target lesion along a straight pathway. The laser emits energy at its tip to ablate a zone of interest at the target location. Ablation can be performed with the assistance of magnetic resonance thermometry (MRT), which provides real-time feedback to the surgeon about the temperature in the ablation zone using a gradient recalled echo sequence.

Because LITT is minimally invasive, it provides faster recoveries and lower morbidity rates than open surgery. However, the success rate for LITT in treatment of patient having temporal lobe epilepsy (TLE) is only 50%, which is significantly lower than the 80% success rate for temporal lobectomies. This is believed to be due to the fact that the straight path of the inserted cannula does not allow access to the entire amygdala and hippocampus with a single insertion, thereby permitting only partial ablation of these structures.

Thus, there is a need for a curved trajectory—both for planning software and for guiding the LITT. There are various planning software available. For example, U.S. Pat. No. 9,818,231 discloses visualization software for intervention. The software display curved pathway with anatomical items. The curved pathway is expressed as spline curve and includes points along the pathway and determines distance between anatomical items and those points.

However, this and similar techniques still have significant limitations. For example, while the curved pathway in U.S. Pat. No. 9,818,231 provides information to provide the patient and to inform the clinician during surgery, it expresses the trajectory as a smooth curve as spline curve. Any actual insertion pathway of an inserted instrument or an instrument shape itself is unlikely to follow this spline curve exactly. Therefore, any plan generated with this software cannot inherently represent the actual pathway of a real intervention and thereby be used to avoid errors during insertion.

Thus, there is need for systems and methods that provide a curved trajectory and use thereof that more closely correspond to the insertion path of a device applicable to guiding interventional tools and instruments (e.g., a catheter) along a curved trajectory during a surgical intervention (e.g., LITT).

SUMMARY OF EXEMPLARY EMBODIMENTS

According to at least one embodiment of the invention, there is provided a planning and visualization method comprising: identifying an entry point and a target volume in a medical image; defining a preliminary curved path between the entry point and the target volume based on a geometric element of the target volume (e.g., a centerline), wherein the preliminary curved path comprises at least two segments, wherein at least one of the at least two segments is an arc segment; modifying the preliminary curved path based on a user input to form a surgical curved path; wherein at least one of the preliminary curved path and the surgical curved path is constrained by a physical parameter of a surgical robot; an displaying at least one of the preliminary curved path and the surgical curved path and displaying the target volume.

In some embodiments, there are two or more concatenated arc segments and at least one straight segment in the preliminary and/or surgical curved path with the straight segment is concatenated between the arc segment and the entry point. One or both of the preliminary curved path and the surgical curved path may be constrained by the physical parameters of the surgical robot. The visualization may include displaying, individually or overlaid on each other or the medical image two or more of: the preliminary curved path, the surgical curved path, the target volume, the geometric element, and distances between the curved path(s) to a boundary of the target volume.

According to other embodiments, there is provided a system for planning and visualizing a curved path comprising: a computer implemented planning and visualization subsystem configured to: identify an entry point and target volume in a medical image; define a preliminary curved path between the entry point and the target volume based on a geometric element of the target volume, wherein the preliminary curved path comprises at least two segments, wherein at least one of the at least two segments is an arc segment; accept user input to modify the preliminary curved path and form a surgical curved path; wherein at least one of the preliminary curved path and the surgical curved path is constrained by a physical parameter of a surgical robot; and display at least one of the preliminary curved path and the surgical curved path and displaying the target volume.

According to yet other embodiments, there is provided a medical planning and implementation system comprising: a computer implemented planning and visualization subsystem configured to perform the method as described herein, and a surgical robot comprising two or more bending sections, wherein the arc lengths of the two or more arc segments are substantially the same as the length of the two or more bending sections.

In other embodiments, there is provided a method of treating a patient having temporal lobe epilepsy (TLE) comprising: identifying an entry point in a medical image of the patient; defining a preliminary curved path between the entry point and a geometric element of the amygdala and hippocampus, wherein the preliminary curved path comprises at least two segments, wherein at least one of the at least two segments is an arc segment; modifying the preliminary curved path based on a user input to form a surgical curved path; wherein at least one of the preliminary curved path and the surgical curved path is constrained by a physical parameter of a surgical robot; displaying at least one of the preliminary curved path and the surgical curved path and displaying the target volume; and providing laser interstitial thermal therapy (LITT) to the patient using a surgical robot comprising two or more bending sections, the LITT provided substantially along the surgical curved path.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Figure 1:
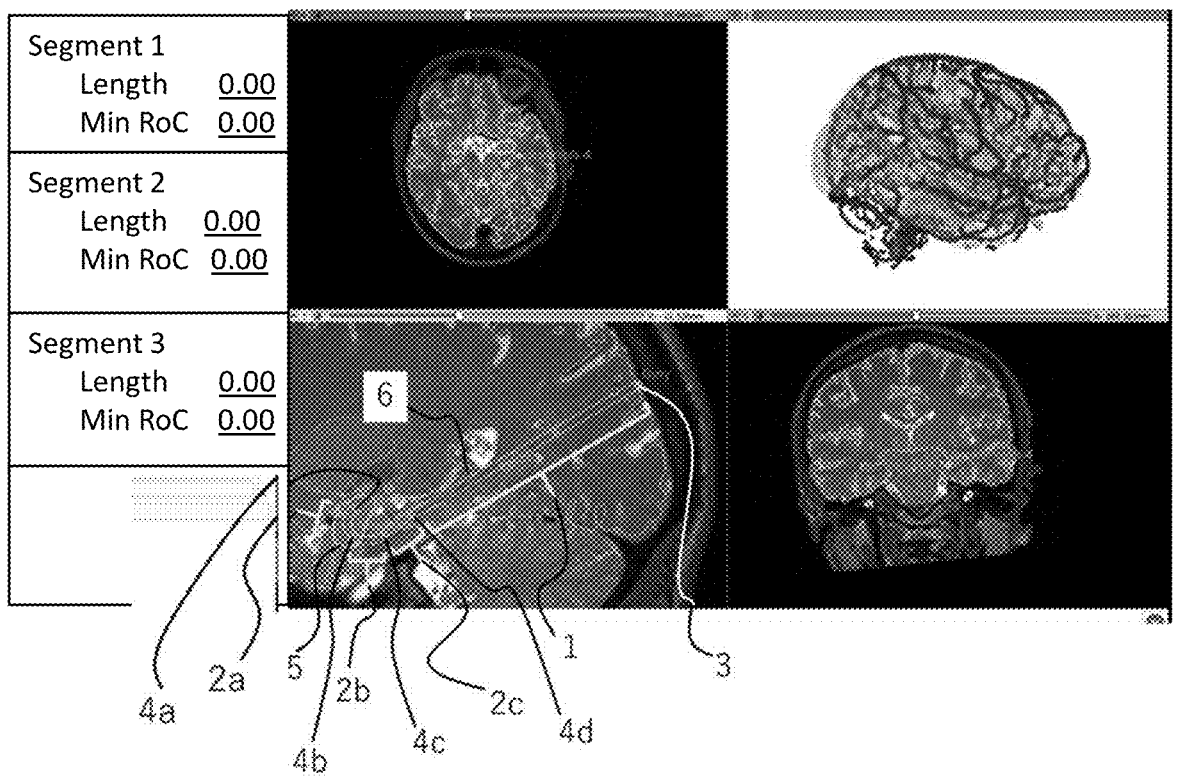
FIG. 1 illustrates a display of an enhanced planning software for brain intervention to a first embodiment of the present invention.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The planning software provide visual information for intervention to the physicians. The display for one particularly embodiment include different views, which may be predefined or set by the user during use (right side of FIG. 1) and control panels for intervention plan (left side of FIG. 1).

The software can display medical images in view ports. In this particular embodiment, the software displays MRI images of the brain.

The operator can identify the target volume by segmenting particular part of MRI images. In FIG. 1, the software segmented amygdala, hippocampus, blood vessels, ventricles, optic tracts, optic chiasm, optic nerves and brain stem, and overlay those segmented models of anatomies with MRI images by using color lines. Specifically, in this embodiment, models of amygdala 5 and hippocampus 6 are target volumes that are the anatomy for LITT procedure to ablate. The operator can also identify volumes to avoid which may be models of the blood vessels, ventricles, optic tracts, optic chiasm, optic nerves and brain stem.

In some embodiments, the target volume is the volume of a three-dimensional model of an anatomical object. For example, the entire hippocampus may be the target volume and be targeted for ablation. In other embodiments, the target volume may be less than the volume of the three-dimensional anatomical object, and in yet other embodiments, the target volume may be greater than that of the anatomical object (e.g., the object and a margin).

The operator can also identify an entry point 3, which may be an entrance point of an ablation instrument through the skull.

By using the segmented anatomies and entry point 3, the physician can simulate insertion and removal pathways while visualizing the medical images, target volume and measurements of distances to structures to avoid and how much of the target volume is reachable to explore an optimal pathway.

These simulated insertion and removal pathways are directed through a target volume, which can be defined as a particular region or point of interest or, more interestingly for some embodiments, an entire volume, such as the whole of the amygdala or hippocampus or the whole of a tumor. Thus, the information on how much of the target volume is reachable can be either indicated visually or calculated and presented numerically during this planning step to help in the optimization process.

The pathways comprises proximal straight segment 1, arc segment 2a, 2b, and 2c. Those segments are concatenated with connection points 4a, 4b, 4c, and 4d.

With the curved pathway, the physician can find an optimal pathway to cover the target volume for ablation in models of amygdala 5 and hippocampus 6, which include complicated longitudinal shape. Also, the physician can find the pathways to avoid critical anatomy by using overlay models with MRI images.

The arc segment 2a, 2b, 2c comprise circular arc with their own arc parameters, which include 1) arc length, 2) curvature radius or bending angle, and 3) bending plane.

In some other embodiments, the arc segments are arc segments of a differentiable curve instead of circular arc. Thus, the arc segments may be arc segments of an ellipse. In other embodiments, the arc segments may be arc segments of a parabola or hyperbola to adjust for, for example, differences in friction between the proximal and distal portions of the bending sections within a bendable catheter. As understood herein, the arc segments, which is either a circular arc segment or a differentiable curve arc segment, has a curvature radius or bending angle that is greater than zero. Preferably, the arc segment has a curvature radius that less than 10 cm.

In some embodiments, the optimal pathway will be defined as described herein. In other embodiments, the optimal pathway may be defined, for example, by a surgeon using the planning system and catheters as described herein. In other embodiments, more objective parameters for optimal pathway may be devised based on the target regions and critical structures to avoid as well as other parameters that are shown to correlate with patient outcome. In other embodiments, the optimal curved pathway may be designed automatically following the work described, for example, by: M. Pinzi, S. Galvan, and Y. B. F. Rodriguez, *Int J Comput Assist Radiol Surg*, vol. 14, no. 4, pp. 659-670, April, 2019; A. Hong, et al., Int J Med Robot, vol. 15, no. 4, pp. e1998, August, 2019 and/or J. Granna, A. Nabavi, and J. Burgner-Kahrs, *Int J Comput Assist Radio Surg*, vol. 14, no. 2, pp. 335-344, February, 2019.

Figure 2A:
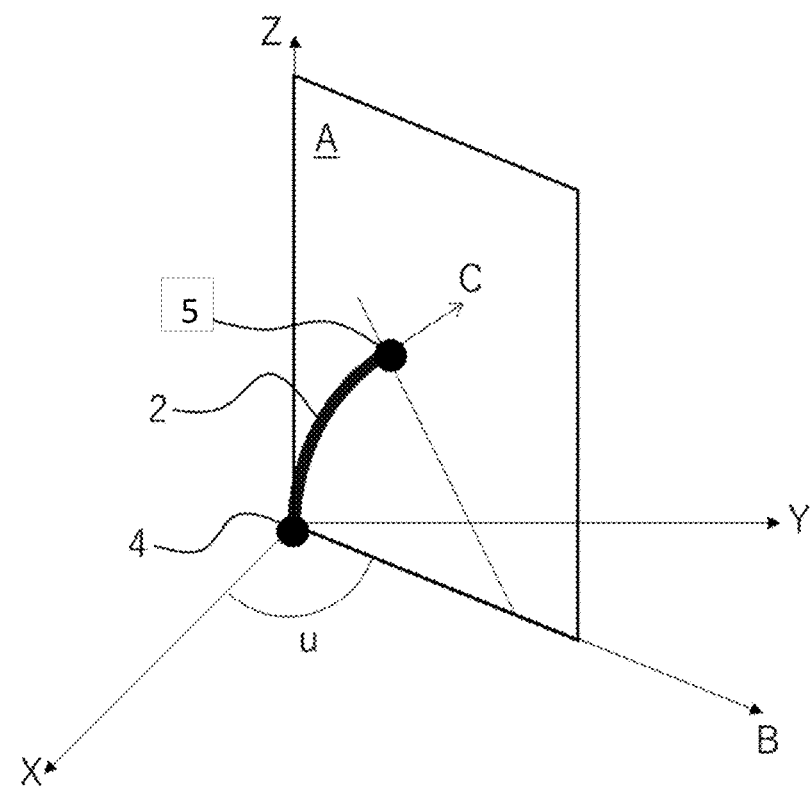
FIG. 2(A) and FIG. 2(B) are drawings showing the arc segment 2 and its arc parameters. One arc segment is a circular arc with connection points 4 at both ends (FIG. 2(A). This arc segment 2 are on plane A with angle u in XYZ coordinate system with origin on one of the connection points, and Z direction as tangent of arc segment 2. Angle u is one of the arc parameters named bending plane.
Figure 2B:
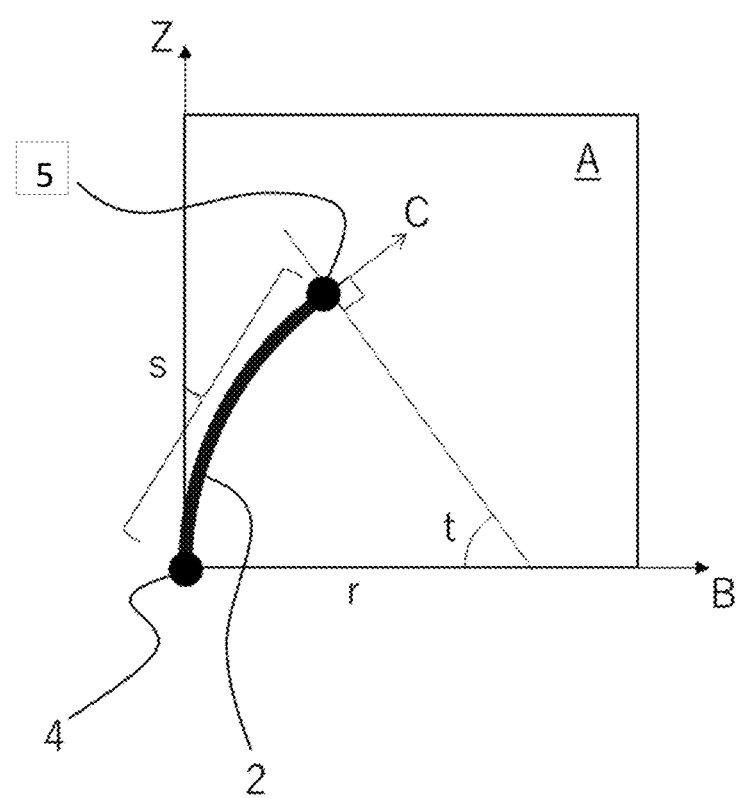

FIGS. 2(A) and 2(B) explain the arc segment 2 and its arc parameters. One arc segment is a circular arc with connection points 4 and 5 at the ends (FIG. 2(A)). This arc segment 2 is on plane A with angle u in XYZ coordinate system with origin on one of the connection points, and Z direction as tangent of arc segment 2 at the connection point. Angle u is one of the arc parameters named bending plane.

On plane A, the arc segment 2 has length of s, and curvature radius r. In FIG. 2 (B), arrow C signifies the orientation vector of the arc segment 2 at connection point 5. The arc length s and curvature radius r are the arc parameters. Also, instead of having a common curvature radius r, arc length and bending angle t, the arc segments 2a, 2b, 2c in FIG. 1 are configured to each have independent arc parameters. However, at connection points between adjacent arc segments, the tangents of adjacent arc segments are identical to maintain curvature continuity.

The operator can change those arc parameters in the software by using control panes 7, 8, 9 for arc segment 2a, 2b and 2c (FIG. 1) and can explore and identify a plurality of curved pathways for the brain intervention.

In the different embodiment, the curved pathway does not include proximal straight segment 1. In this embodiment, the curved pathway includes only arc segments 2 from entry point 3 to target volume 5 and 6.

Figure 3A:
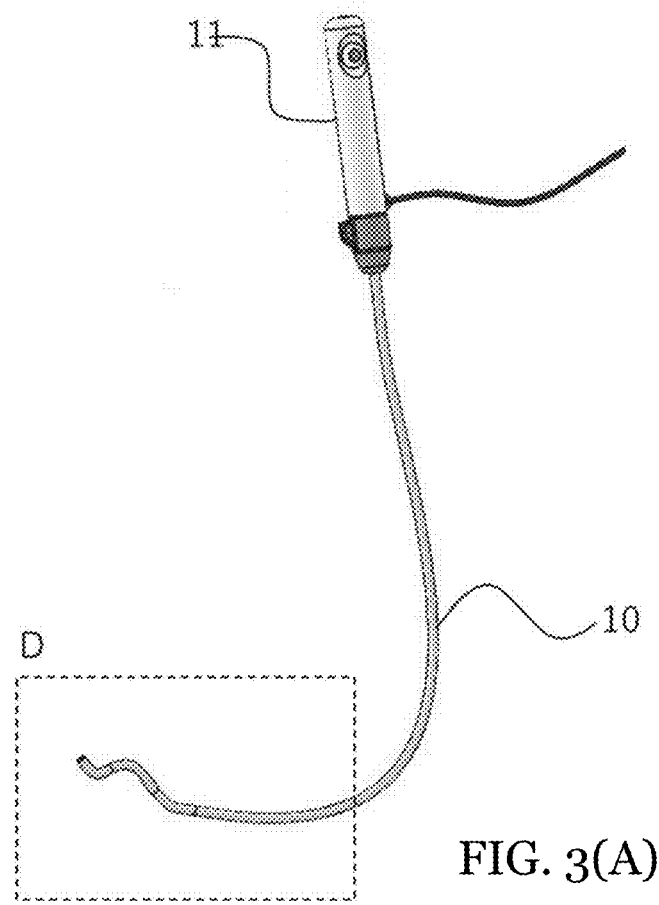
FIG. 3(A) and FIG. 3(B) illustrate bendable catheter subsystem to a second embodiment of the present invention.
Figure 3B:
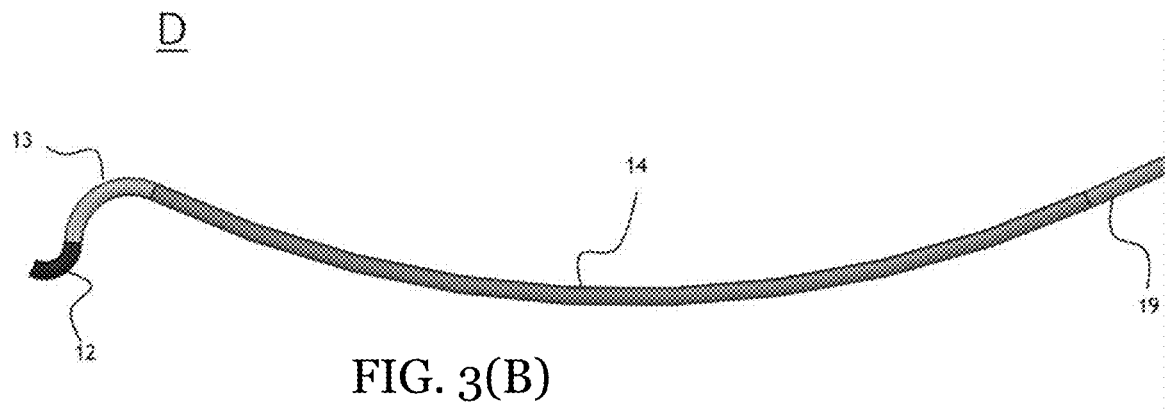

While FIGS. 2(A) and 2(B) show single arc segments, other embodiments are shown in FIGS. 3(A) and 3(B) where an exemplary bendable catheter subsystem is described. The bendable catheter subsystem form intervention system in conjunction with planning software as described above. The bendable catheter subsystem comprises bendable catheter 10 and control handle 11.

Control handle a includes bending means to bend bending sections in bendable catheter 10. The bending means can be motors or mechanical structure configured to transmit forces from the operator.

The bendable catheter includes three bending sections 12, 13, 14 with proximal section 19. The three bending sections 12, 13, 14 can be bent three-dimensionally with control handle 11. The proximal part 19 can be either passively flexible or rigid with straight profile. In some embodiments, each of the bending sections has two or three guide wires that provide both push and pull actuation of the bendable section with the control handle 11. In some embodiments, the proximal section 19 is passive in that there are no tendons or guide wires to control the orientation of the section. However, there is some flexibility in the section that allows the section to move to reduce the friction within the bendable device and/or better follow the direction of the bending sections as they are manipulated within a lumen.

Specifically, in this embodiment, the software has fixed parameter of the arc length s corresponding to lengths of the bending section. Also, while the bendable catheter 10 includes maximum bendable curvature radius, the software is able to automatically limit the curvature radius within this maximum bendable curvature radius in the planning procedure, so that the physician can eliminate non-feasible plan for the intervention.

In other similar embodiments, instead of having three bending sections 12, 13, and 14 and a proximal section 19, the bendable catheter subsystem may have, for example, 2, 4, 5, 6or more bendable sections. Additional bendable sections may be provided to give greater flexibility and ability to navigate a torturous path. While the bendable catheter subsystem shown in FIGS. 3(A) and 3(B) are designed to have a small outer diameter that is preferred for, for example, brain surgery, other embodiments are not as constrained to have as small a diameter, and additional control wires and thus bendable sections can be added based on the catheter as described above. Similarly, other configurations of a bendable catheter subsystem may be used with more or less bendable sections or with additional non-bendable or passive sections.

Since the bending sections (either the three provided or more or fewer as appropriate) can be approximated with circular arcs respectively, the software can create feasible and accurate pathways which can be followed by the actual bendable catheter.

In use, the bendable catheter subsystem can be manipulated by, for example, independently bending bendable section 12 and bendable section 13 as well as bending bendable section 14. Thus, in the planning stage, a curved pathway that comprises three concatenated arc segments where the length of the arc segments corresponds to the length of the bendable sections 12, 13, and 14 and a straight section corresponding to section 19 provides a useful planning trajectory that can be followed with the bendable catheter subsystem during a surgical intervention such as LITT or tumor ablation therapy.

In some embodiments, the bendable catheter subsystem is described by one or more of U.S. patent Publications 2018/0296800; 2019/0105468; and 2020/0383,670 and U.S. patent Ser. Nos. 10/687,694; 11/007,641; 11/051,892; 11/096,552; 11/103,992; and 11,278,66, each of which are incorporated by reference in their entirety.

Exemplary Study

Laser ablation systems for LTE and other neurosurgical applications are available and include Visualase (Medtronic, Inc.) and NeuroBlate (Monteris, Inc.). Both systems use straight cannulas to access the brain lesion with one channel in the cannula dedicated for the laser fiber and a second channel for the cooling system. The insertion paths have generally been planned in 2D cross sections of preoperative MRI. The insertion path has been typically designed preoperatively by placing one path endpoint inside the target and one on the skull surface. The entire path can be viewed relative to the target and other brain structures of interest by scrolling through 2D cross sections of the MRI images either in conventional axial/sagittal/coronal views or in orthogonal views aligned with the path (inline) and perpendicular to the path. The path can also be viewed in a 3D view as a cylinder relative to segmented structures of interest. FIG. 1 shows a custom path planning system for straight path insertion implemented as a Python module in 3D Slicer for this study. Surgeons adjust path endpoints to find a path that provides as much coverage of the target lesion as possible (e.g., the amygdala and hippocampus for LTE or the tumor for tumor ablation) while avoiding critical structures (e.g., blood vessels, the ventricles, optic tracts, etc.). Unfortunately, because of the geometric complexity of structures in the brain and the shape of the lesion, it may be impossible to cover the entire lesion while avoiding critical structures with a single insertion of the laser with this straight path insertion geometry. When considering multiple insertions, surgeons must balance trade-offs between optimal treatment and the risk of hemorrhage or functional deficit. The path can be edited and viewed 2D in conventional axial/sagittal/coronal views or inline/perpendicular views. End points can be selected and dragged in 2D or 3D.

Curved Insertion Paths

Current embodiments provide for curved insertion paths and can also include, for example, the bendable catheter subsystem as described in FIGS. 3(A) and 3(B). These curved insertion paths facilitate better access to brain lesions by LITT with better avoidance of critical structures during insertion of the laser into the brain. Additionally, using planning software that provides arc segments to define the curved trajectories correspond more closely to the actual movement and location of the bendable catheter subsystem as compared with more generalized curved trajectories.

Figure 3C:
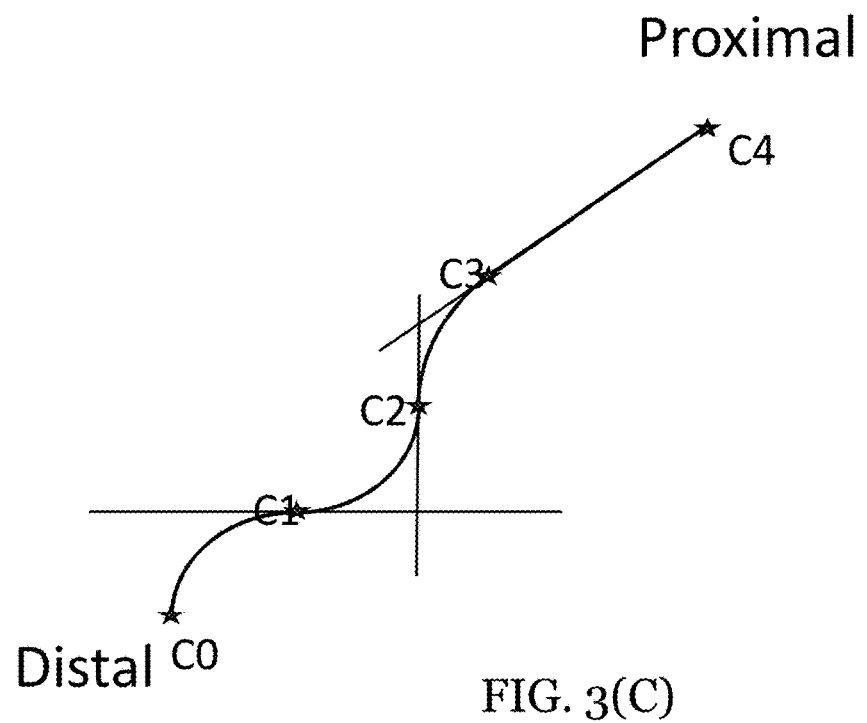
FIG. 3(C) is a drawing showing three arc segments and one straight segment between distal and proximal ends.
Figure 3D:
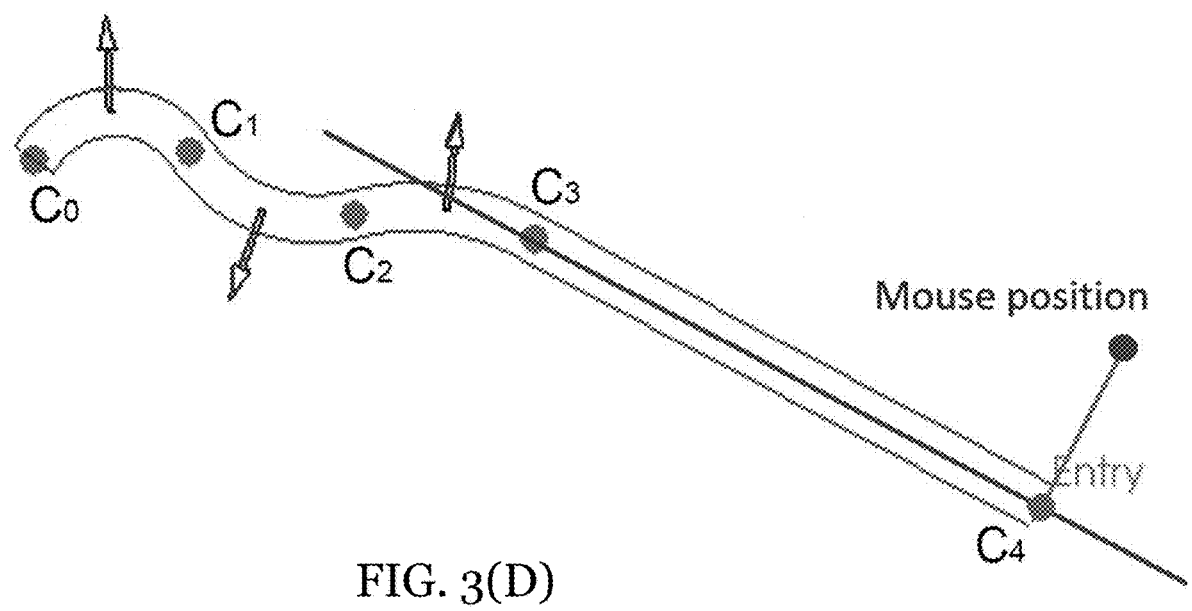
FIG. 3(D) shows a similar curve but within a model for a robotic catheter model.
Figures 4A, 4B, 4C, 4D, 4E, 4F, 4G, 4H:
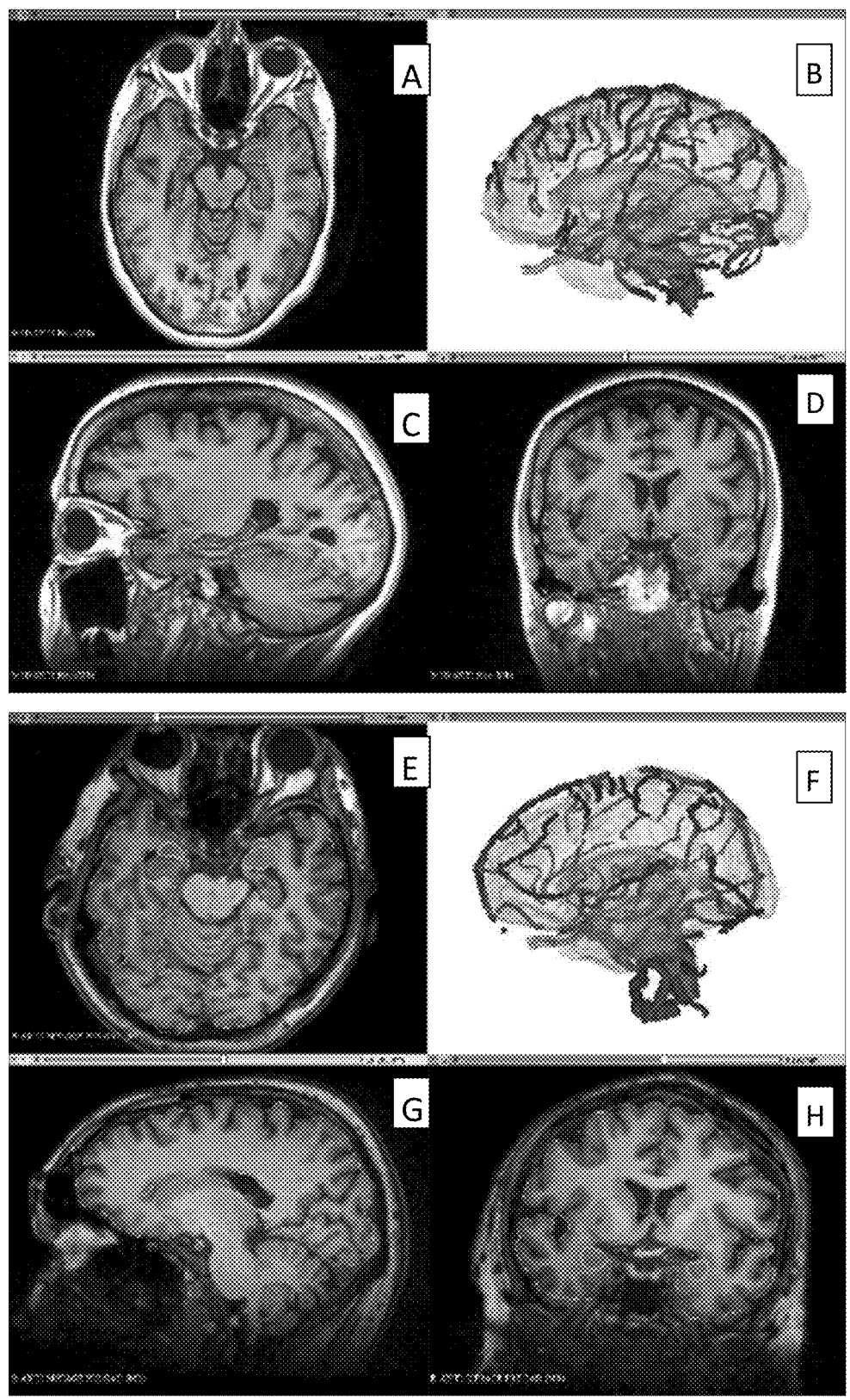
FIGS. 4(A)-4(P) are screen shots using various embodiments of the planning system for laser ablation therapy showing an exemplary LTE cases with segmented amygdala, hippocampus, blood vessels, ventricles, optic tracts, optic chiasm, optic nerves and brain stem.
Figures 4I, 4J, 4K, 4L, 4M, 4N, 4O, 4P:
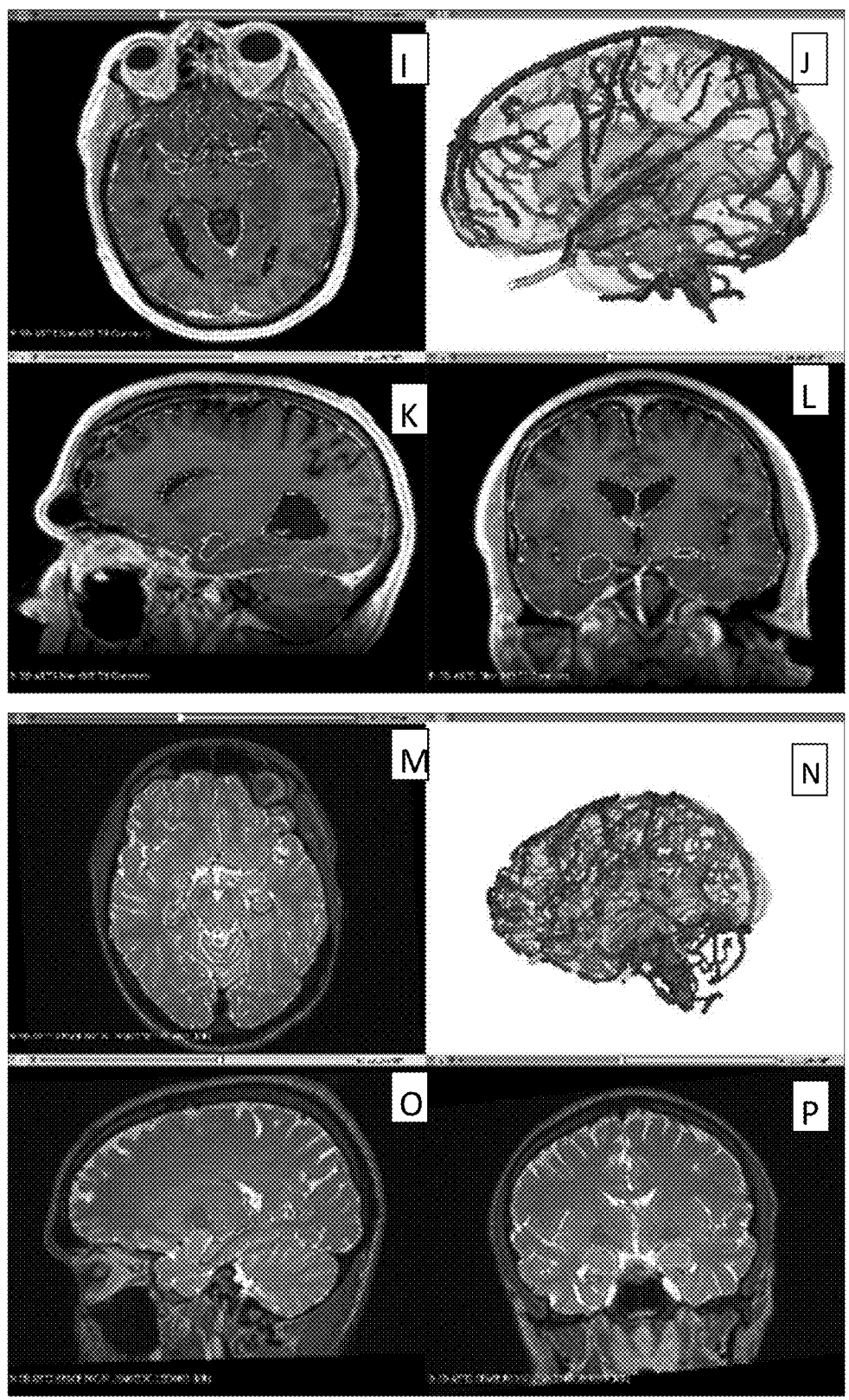
Figures 5A, 5B, 5C, 5D:
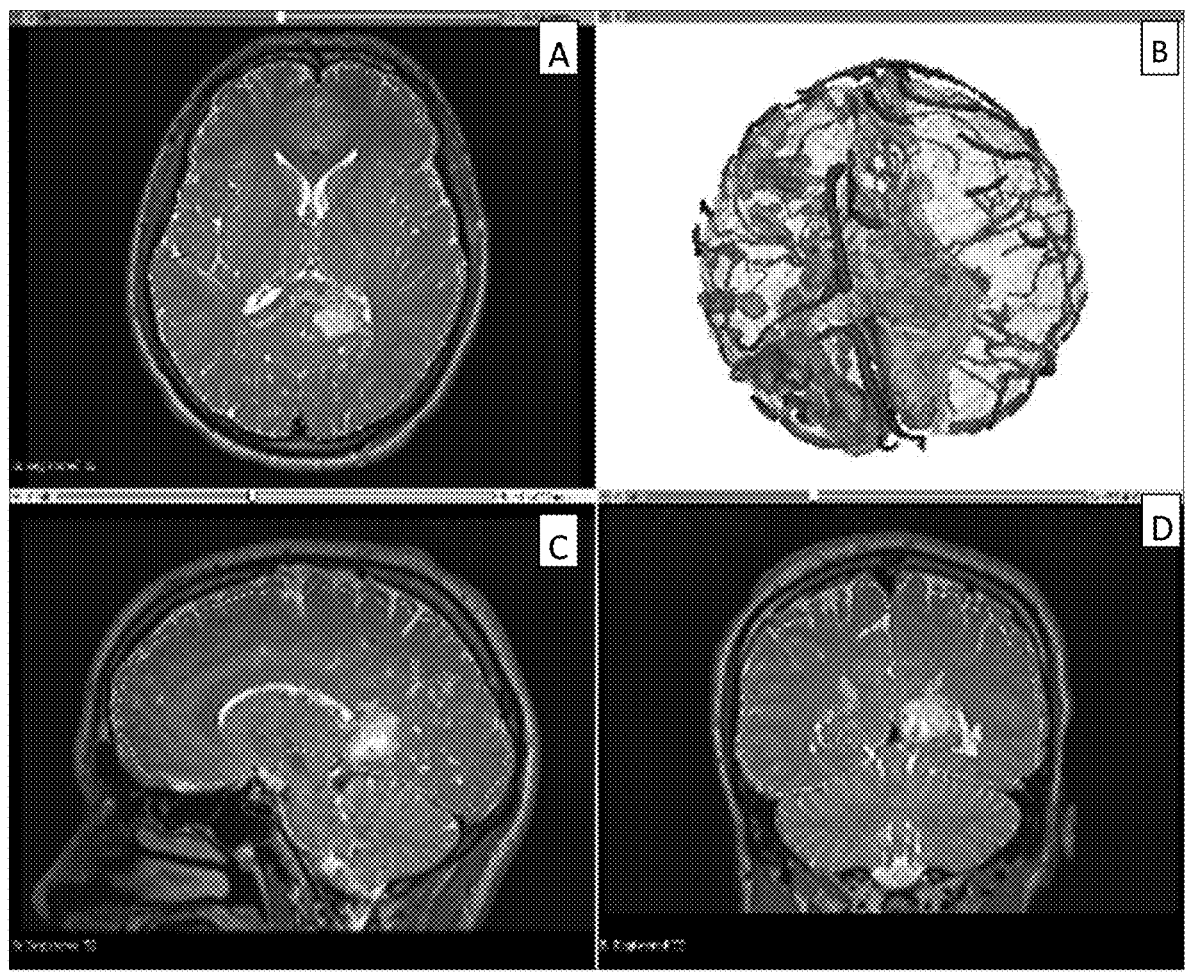
FIGS. 5(A)-5(D) are screen shots of an embodiment of the planning system for the tumor case with segmented tumor, ventricles, brainstem, functional language regions (via fMRI) and white matter tracts (via dMRI).
Figures 6A, 6C, 6E, 6G:
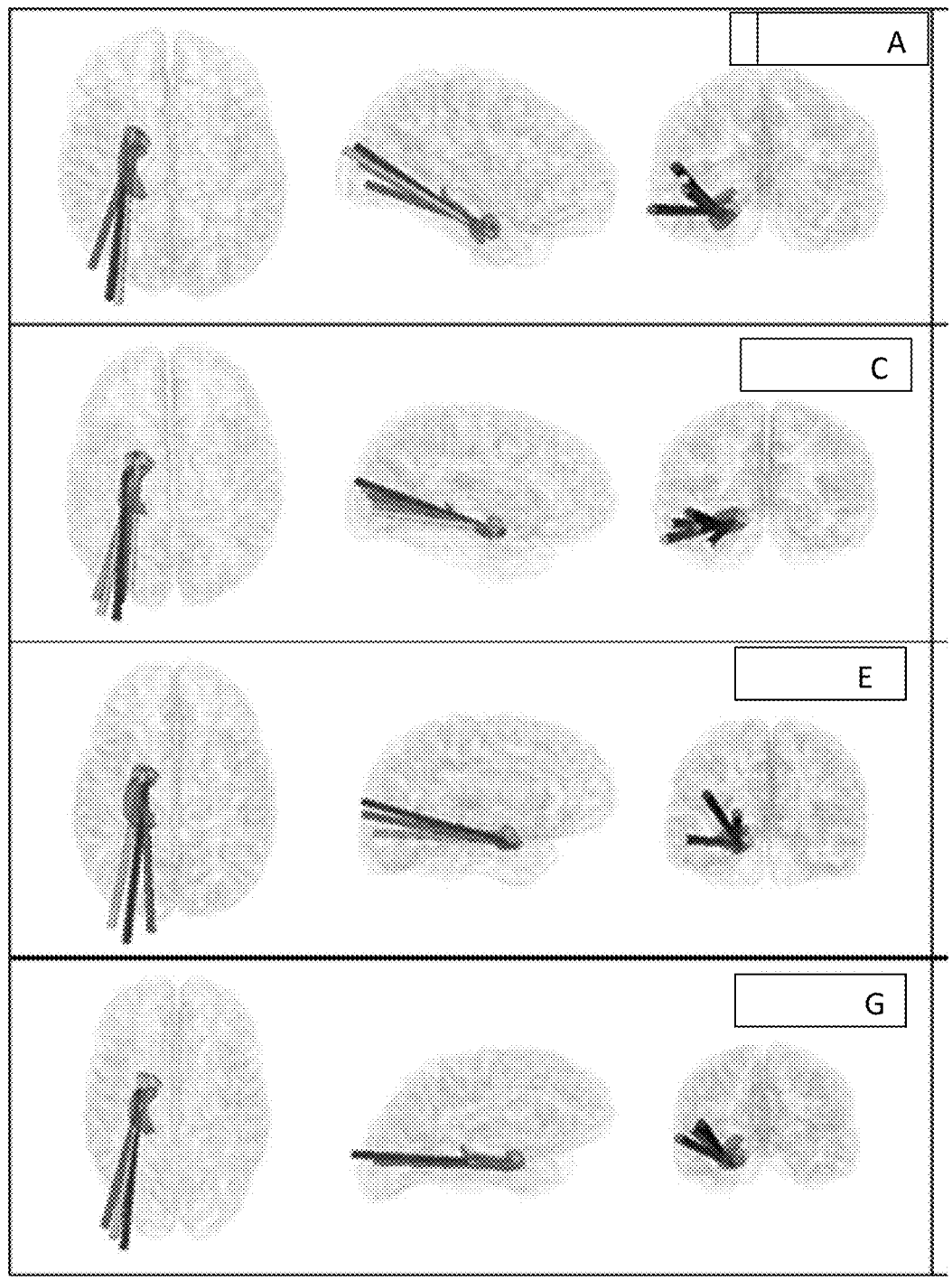
FIGS. 6(A)-6(H) shows three views of straight paths designed by neurosurgical residents.
Figures 6B, 6D, 6F, 6H:
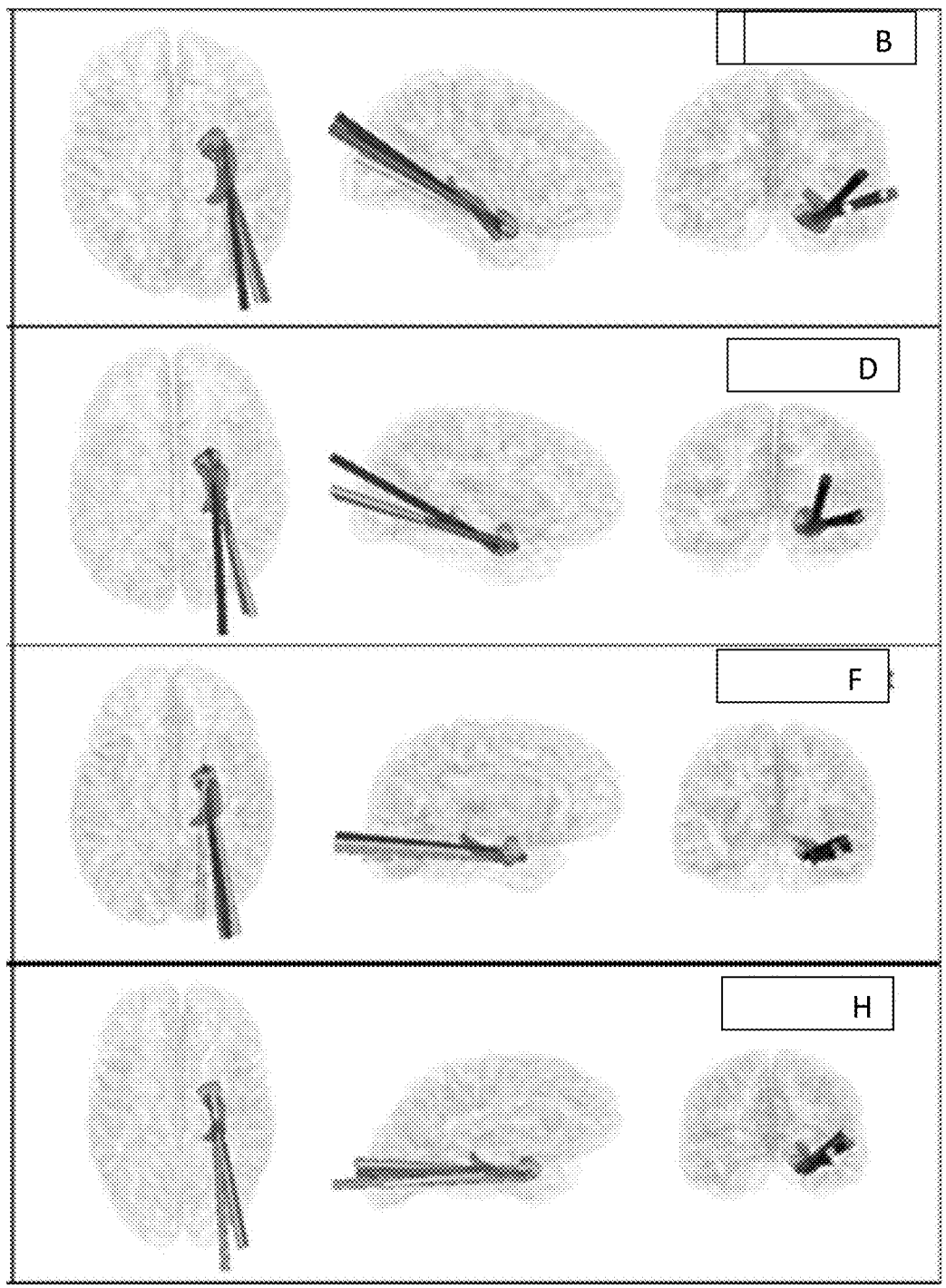

The curved insertion paths include one or more concatenated arcs. (For example, the concatenated arcs between point C0 and C1; C1 and C2; and C2 and C3 in FIG. 3 (C). The curved insertion paths may also include a straight section such as shown between point C3 and C4 in FIG. 3(C). In some preferred embodiments, a straight section is used from the skull entry point to a point at or near the target (e.g., a brain lesion) and then two or more concatenated arcs provide a path through the lesion. This can be seen in FIG. 3(D) which provides the three concatenated arcs and the longer straight section extending from the entry point to C4 in FIG. 3(D).

Study

A study was performed using retrospective data from four epilepsy patients and one deep brain tumor patient. Four clinicians planned conventional straight insertion paths for the left and right sides of the LTE patients and for the tumor case (9 total paths per clinician). Two technical experts used an enhanced version of the path planning system to manually plan optimal curved insertion paths for the same cases. Differences between straight and curved insertion paths were analyzed to quantify the advantages of curved insertion paths over straight insertion paths. Insertion paths were assessed based on the percentage of the lesion covered and distances from the path to the closest critical structures.

This retrospective study included 5 patients who received LITT treatment in 2019 at the Brigham and Women's Hospital. Image data available for each patient is shown in Table 1, which includes target and image data available for cases in this study. Images were acquired for clinical indications and hence are not consistent across the study. Target structures (i.e., the left and right amygdala and hippocampus for each LTE patients and the brain tumor for the tumor patient) and critical structures to be avoided (e.g., blood vessels, ventricles, optic tracts) were segmented using the BrainLAB Elements Segmentation Cranial software. The automatic atlas-based segmentation in this system provides accurately labeled structures from several MRI protocols [J. F. Daisne, and A. Blumhofer, *Radiat Oncol*, vol. 8, pp. 154, Jun. 26, 2013]. Segmentations were then exported to 3D Slicer and used to create closed surface meshes using the 3D Slicer Segment Editor module [C. Pinter, A. Lasso, and G. Fichtinger, *Comput Methods Programs Biomed*, vol. 171, pp. 19-26, April, 2019.]. Segmented objects were displayed in a 3D scene and in 3 cross-sectional 2D views. Representative cross-sections and the reconstructed 3D models of relevant structures (target lesions and critical structures to be avoided) for each case are shown in FIGS. 4(A)-4(P) and 5(A)-5(D).

TABLE 1

| Case | Target | Preoperative image data available |
| --- | --- | --- |
| LTE1 | Amygdala/hippocampus | MRA, MRI T1 w/o contrast |
| LTE2 | Amygdala/hippocampus | MRI T2 for non-enhancing lesions |
| LTE3 | Amygdala/hippocampus | MRI T1 with gadolinium |
| LTE4 | Amygdala/hippocampus | MRI T1 w/o contrast |
| BT1 | Tumor | MRI T1 and T2 |

Path Planning System

A planning system was created using an exemplary custom 3D Slicer module in Python for neurosurgeons to plan the insertion paths for this embodiment. The module includes an interactive graphical user interface (GUI) that provides tools for displaying cross-sectional images and 3D models and for planning the insertion path (FIGS. 1 and 4). The path is designed by placing a pair of landmarks corresponding to the tip of the laser and the entry point on the skull, with the line joining these two points defining the insertion path of the cannula for LITT. A 2.5 mm radius cylinder representing the cannula is placed along the path and a 2.5 mm radius sphere is placed at the tip of the laser to represent the ablation zone. The radii of the cannula and the ablation zone can be adjusted via the GUI. Users can edit the laser tip and entry point positions in the axial, sagittal and coronal views, and in the 3D view. 2D cross sections can be viewed in conventional axial/sagittal/coronal views or in views that are perpendicular and parallel to the insertion path. The insertion path can be edited in any 2D view by selecting and dragging the ellipse representing the intersection between the cylinder and the current slice. This action then re-computes the path entry point, keeping it on the skull surface.

Enhanced Path Planning System for Curved Insertion Paths

The enhanced planning system incorporates constraints of a wire-driven multi sectional surgical robot, such as the surgical robot described in [Y. Gao, K. Takagi, T. Kato, N. Shono, and N. Hata, *IEEE Trans Biomed Eng*, Apr. 29, 2019]. The exemplary robot is composed of a 3.5 mm diameter Nitanol tube, regularly cut to create flexible segments. Each segment is linked to its neighbors with a rigid section allowing segments to bend in different planes. Bent segments form roughly circular arcs of fixed length and maximum curvature. Push-pull wires responsible for the bending of the robot are inserted in wire guides regularly distributed in the walls of the tube. Each section has one wire guide and each wire guide is fixed at the distal end of its section. Guide wires are connected to an actuation system with one motor per wire. This robot uses a Follow-the-Leader motion algorithm to minimize strain on brain tissue during insertion. The tube has a 2.5 mm diameter inner channel that could be used to house a fiber optic laser for LITT. In other embodiments, other surgical robots may be used instead, and the constraints of these systems may be incorporated in the enhanced planning system as describe herein. Other wire-driven multi-sectional surgical robots may be described, for example, in U.S. Pat. Publications 2015/00088161; 2018/0192854; 2018/0296800; 2018/0310804; 2018/0243900; 2018/0311006; 2019/0015978 and 2019/010546 and PCT publication WO2018204202.

To emulate the constraints of this robot, the path planning systems as provided herein allow users to design a path composed of multiple straight and curved segments. Each segment can form a circular arc constrained to a single plane. The number of segments and length and maximum curvature of each segment are customized in the GUI. Tangents at the junction of two consecutive sections are constrained to have equal magnitude so the path is continuous. Paths are planned by editing segment parameters and dragging segment endpoints in 2D cross-sectional views or the 3D view. In some embodiments, paths are designed by free-hand drawing a path in 2D and then running a custom algorithm to position segment endpoints and curve planes to optimally fit the free-hand path. The resultant path can then be edited by dragging segment endpoints.

This system is useful but may not be preferred for non-technical clinicians. Added to the complexity of moving segment endpoints in 3D, a 3D curve cannot be visualized in a single 2D cross-section, requiring visualization and manipulation in the 3D view, something that some clinical users were not comfortable with. For this reason, in this preliminary study, optimal curved paths to be compared with straight paths were planned by technical users.

Straight Path Planning

Four clinicians with experience planning multiple LITT cases using commercial software, including a neurosurgery resident, two neurosurgery fellows and a neurosurgery post-doctoral researcher, participated in this study. Each clinician was asked to plan a conventional straight insertion path for each side of the LTE patients (8 trajectories per clinician) and for the tumor case using the straight path planning system described above.

After an introduction about the 3D Slicer controls and features available in the straight path planning system, the clinicians were free to interact with each case. Clinicians were asked to voice their thoughts during planning so that we could get a better understanding of their priorities and what structures they were trying to avoid. For each trajectory, end points were saved for later intra-operator comparisons and assessment of path quality.

Curved Path Planning

Two technical experts used an enhanced version of the path planning system to manually design optimal curved insertion paths for the same cases used for straight path planning. Users were able to vary the number, length and maximum curvature of each segment in order to achieve an optimal path. Based on feedback from the clinical users about their targeting priorities and what structures they were trying to avoid, two approaches for the curved path were considered: (1) Straight access from the skull to the target followed by a curved insertion into the target structure, and (2) Curved access and insertion into the target structure.

Path Assessment

Path quality was assessed for this exemplary study based on two metrics:

(1) How much of the lesion was covered by the planned insertion path, where, in this study, coverage assumes a laser ablation radius of 1 cm about the laser tip and it is assumed that the laser can be fired at multiple positions as it is withdrawn, resulting in the ability to achieve up to a 1 cm cylindrical ablation zone along the path.

(2) How closely the planned insertion path approaches nearby structures deemed to be critical by clinicians in this study and two senior neurosurgeons. In this study, each insertion path was sampled at 1 mm intervals along their entire lengths and distances to nearby critical structures were measured. Critical structures for the LTE cases included the segmented ventricles, blood vessels, sulcal folds, optic tract, optic chiasm, and brain stem. Critical structures for the brain tumor case included blood vessels, the ventricles, language regions defined by functional MRI (fMRI), and the splenium, inferior longitudinal fasciculus and inferior frontal-occipital fasciculus white matter tracts identified by diffusion tensor imaging (dMRI) (see FIG. 3).

To compare quality, we had to define metrics for measuring coverage and safety. For coverage, we segmented voxels of the target structures, here the amygdala in green and the hippocampus in pink. We defined the ablation region to be the volume of the target structure that lay within a specified distance from the insertion path. We defined the target coverage to be the percent of voxels of the target that lay within the ablation region. We measured target coverage for distances of 5 and 10 mm from the insertion path. These distances represent a typical range of ablation radii for LITT.

For safety, we computed distance fields for each critical structure to be avoided by the insertion path. We then sampled the distance to each critical structure at 1 mm intervals along the insertion path. We recorded both the minimum distance from the insertion path to each critical structure and the lengths of the path that lay within 5 mm and 10 mm of each critical structure.

These simple measurements do not give a perfect measurement of coverage or safety and there are multiple factors that they ignore. However, they provide some understanding and can both be computed in real time to provide immediate feedback as the insertion path is being designed.

The straight paths planned by each clinician and the curved paths according to embodiments as disclosed herein were defined by technical experts for each of the 9 cases. It was found that the curved paths provided improvements as compared to the straight paths. For example, there is better coverage of the lesion with a smaller ablation radius with the curved path.

Figure 7:
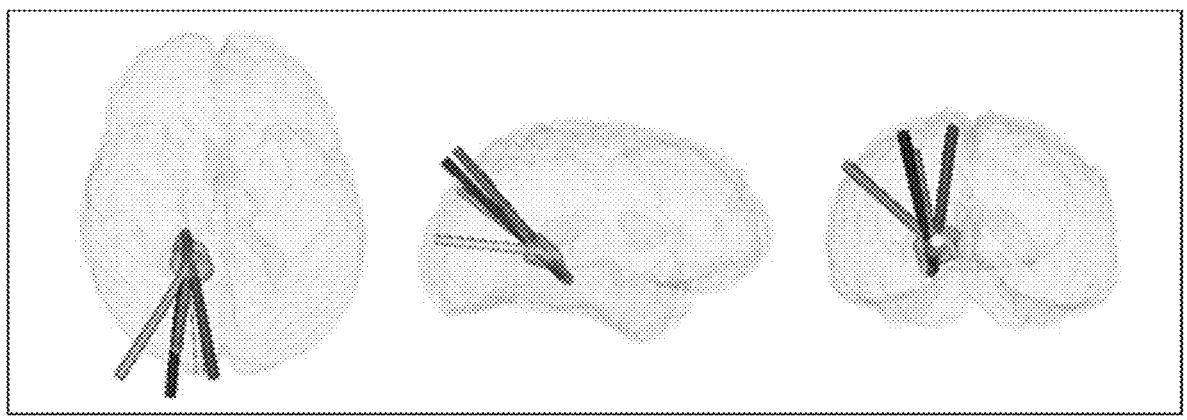
FIG. 7 shows the actual path used in surgery to reach the amygdala and hippocampus for treating MTLE after the design phase shown in FIGS. 6(A)-6(H).
Figure 8A:
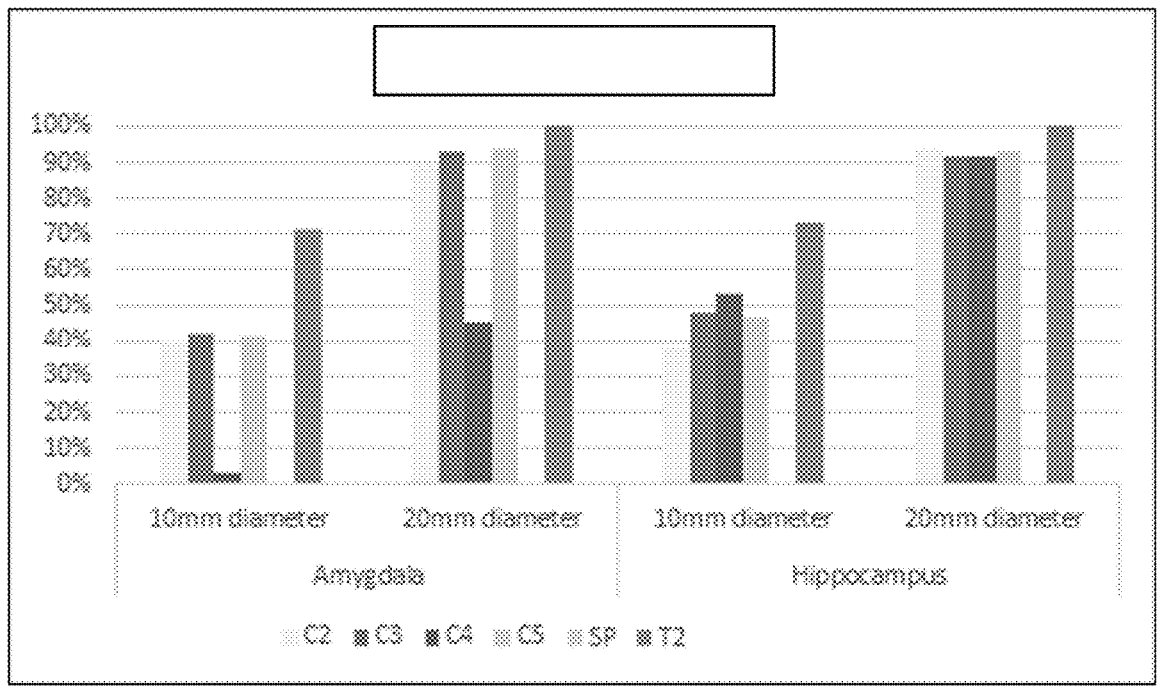
FIGS. 8(A)-8(C) are charges showing the coverage of the surgical paths of FIG. 7 for coverage for temporal lobe epilepsy in the amygdala and hippocampus, $TLE_1$ Right (FIG. 8(A)), and $TLE_1$ left (FIG. 8(B)). The tumor coverage is shown in FIG. 8(C).
Figure 8B:
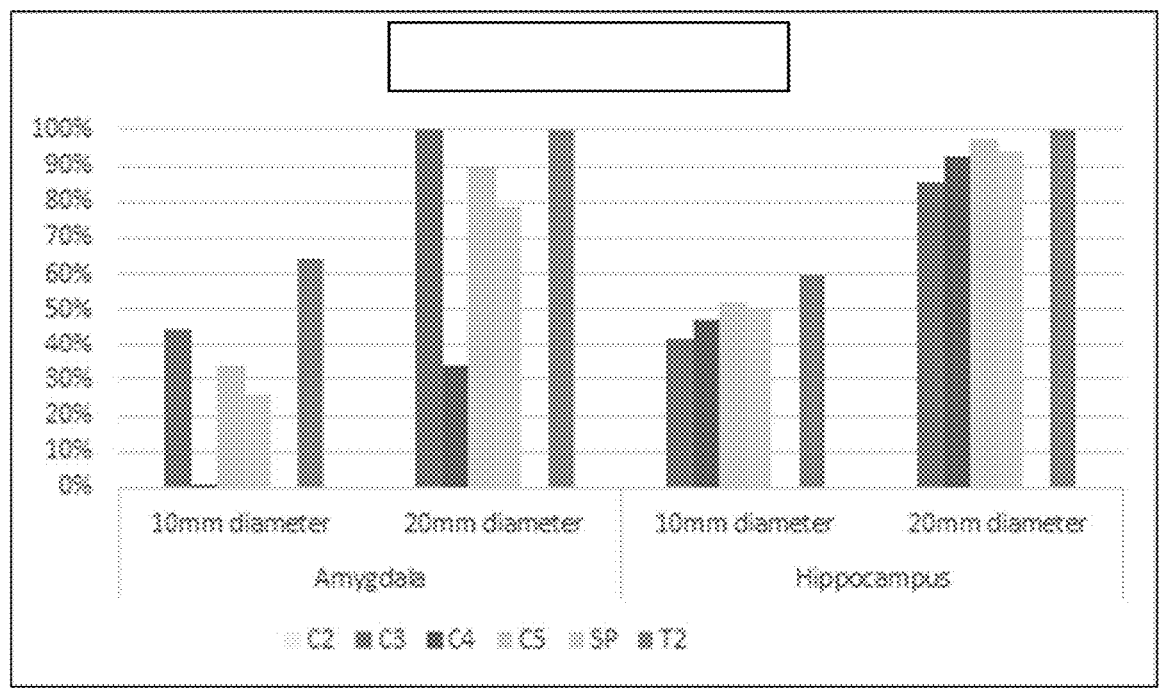
Figure 8C:
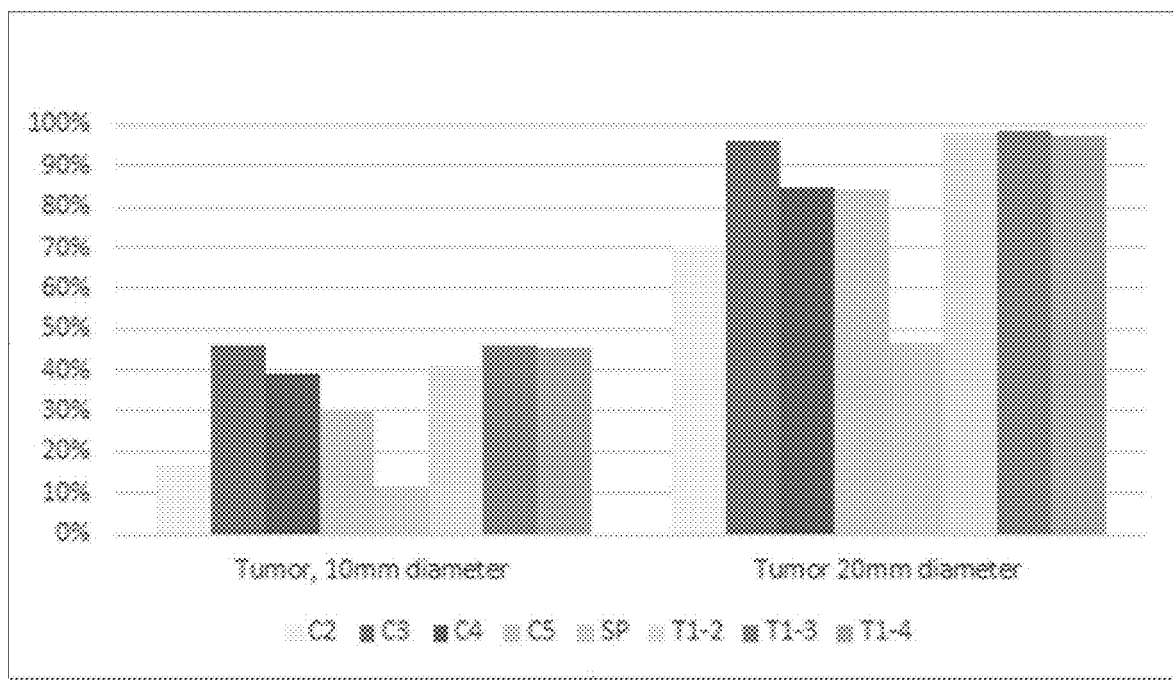

FIGS. 6(A)-6(H) show straight paths designed by neurosurgical residents and the actual path used in surgery to reach the amygdala and hippocampus for treating MTLE. We observed relatively little variation in these paths likely because, in the MTLE cases, the entry and target points are highly constrained by the shapes and locations of the targets and surrounding critical structures. In contrast, paths to the tumor shown in FIG. 7 showed more variation. In this case, access to the target tumor was less highly constrained. Also, because the tumor curved in two dimensions it was not possible to reach the entire tumor with a single straight insertion path. Thus clinicians used different strategies to try to reach as much of the tumor as possible to optimize coverage.

Predicate to Path Planning

To optimize the system and to minimize the time and technical skill involved in path planning of a curved path, a preliminary curved path can be provided. This preliminary curved path (which may include a straight section and includes one or more, or two or more concatenated arcs) can be modified by the clinician to provide the planned path. Thus, in some embodiments, to create a preliminary curved path, a geometric element is used to define the path to the target area (e.g., the amygdala, hippocampus, or other organ) is defined and used as part of the initial proposed path.

Geometric element can be, for example, a centerline, a surface, a distance field, or a label map. In one embodiment, the geometric element is the centerline of the target area. For example, the target volume (e.g., a combination of the amygdala and hippocampus) could be determined by segmenting the target structures. A centerline of the target volume could then be determined to specify an initial proposed path (the preliminary curved path). Further, the minimum and maximum distances from the centerline to the boundary of the target volume could be defined at each point along the centerline to provide boundaries for an initial ablation radius at each point.

In the present embodiment, a centerline of the target volume provides a reasonable path for accessing as much of the target volume as possible, assuming the laser ablates a spherical volume of tissue about its tip location. Because the shape of the target volume and its centerline may have complex curvature in 3 dimensions, providing this initial proposed path with a simple GUI that enables the surgeon to make minor modifications to the initial proposed path could substantially simplify the task of defining an optimal curved path.

In some embodiments, the preliminary curved path is calculated based on the concatenated arc structure and the physical parameters of the surgical robot such as the wire-driven multi sectional surgical robot shown in FIG. 3(B) and described herein. This surgical robot has pre-defined lengths for each of sections 12, 13, 14, and 19, maximum curvature, and diameter of each of the sections in the robot. The limitations that the particular surgical robot to be used in surgery can be used to constrain the preliminary curved path so that a surgical reproduction of that path is possible. In some embodiments, the constraints of the preliminary curved path are more limiting than is allowed by the surgical robot. For example, it could be preferred to limit the potential arc curvature to a percentage (e.g., 70%, 80%, 90%) of the maximum curvature for the preliminary curved path to provide for a less stringent initial route and the ability to adjust that path with increased curvature if indicated by the clinician and still be within the constraints of the physical parameters of the surgical robot. The constraints may be of a single type of physical parameters (e.g., the maximum curvature of the various arc segments) or may be of two or more physical parameters (e.g. the maximum curvatures and the lengths of the various arc segments).

The number of straight segments, if present, and the number of concatenate circular arcs may be fixed based on the surgical robot to be use, or they may be allowed to be adjusted by the clinician. For example, there may be two arcs and one straight segment, or there may be three arcs and one straight segment. In other embodiments, four or five arcs may be used. In yet other embodiments, the segments may comprise one arc, one straight segment and then another arc segment. Each arc segment can form a circular arc constrained to a single plane. The number of segments and length and maximum curvature of each segment are customized in the GUI. Tangents at the junction of two consecutive sections are constrained to have equal magnitude so the path is continuous.

The preliminary curved path may be calculated based on the geometric elements and optionally the physical parameters of the surgical robot automatically, for example as the centerline of the target structure. In another example, an automatic method might determine a set of circular arcs and straight segments that approximate the centerline. In a third example, an automatic method might incorporate additional constraints or objectives including geometric constraints of the surgical robot or distances from the curved path to structures to be avoided.

In other embodiments, the preliminary curved path is created semi automatically, for example by providing an initial proposed path in a planning system and a GUI that enables a clinician to modify the initial proposed path. The planning system could provide visualizations of the path in the context of medical images, the target volume, segmented structures to avoid, and measurements of distances to structures to avoid and how much of the target volume is reachable.

In some embodiments, it is advantageous to begin with a preliminary curved path since, if the clinician is to create a surgical curved path without this initial pre-pathway, the refinement of the path is constrained in multiple dimensions and is either requires a substantial skill set or time to create a path.

After the preliminary curved path is calculated, this path can be shown to the clinician and the clinician is given the option to modify the path to create a surgical curved path. The modification of the preliminary curved path may be constrained to limit the surgical curved path based on the physical parameters of the surgical robot such as the wire-driven multi sectional surgical robot shown in FIG. 3(B) and described herein. This surgical robot has pre-defined lengths for each of sections 12, 13, 14, and 19 and maximum curvature of each of the sections in the robot and these physical parameters may be used to constrain the preliminary curved path and/or the surgical curved path.

While both the preliminary curved path and the surgical curved path may be constrained based on the physical parameters of the surgical robot, at least one of the curved paths must be so constrained. The physical parameters of the specified surgical robot to be used in surgery can be used to constrain one or both of the curved paths so that reproduction of that path during surgery is optimized or at least possible. The at least one of the preliminary and surgical curved paths may be constrained at any point in the process. For example, it may occur after defining the centerline (or other geometric parameter), after the clinician modifies the preliminary path to the surgical path, or concurrently during the formation of the preliminary and/or surgical paths. For the surgical curved path, the modifications allowable by the user may be constrained based on the physical parameters of the surgical robot. Alternatively, fewer constraints may be placed on the user modification and an additional step of adjusting the surgical curved path to fit the constraints of the surgical robot may occur after the user makes the modification(s). This may also be an iterative process between user modification and review and/or adding constraints based on the physical parameters. Additionally, in some embodiments, one or more of the physical parameters may be used to constrain the user modifications and other physical parameter(s) may be included at a different time during the process.

In embodiments where only the preliminary curved path is constrained by the physical parameters of the surgical robot, a parameter may be provided to the clinician to describe how far the adjustments used to create the surgical curved path moved the planning away from the optimal performance of the surgical robot. This optimal performance may be, for example, the actual limits of the surgical robots or, for example a percentage of that performance (e.g., go % of the maximum curvature available in an arc segment).

Methods of Treating the Amygdala and Hippocampus

In some embodiments, there are provided methods of treatment of temporal lobe epilepsy (TLE) where the amygdala and hippocampus are targeted using a curved trajectory and then treated using LITT therapy. While treatment of TLE is known, the present invention provides a minimally invasive treatment. The curved pathway provides for access to the entire amygdala and hippocampus with a single insertion of a bendable device such that the entire necessary area can be ablated with the LITT therapy. The curved pathway further allows for the avoidance of the critical structures between the entry point and the amygdala and hippocampus.

It has been found that the curved path consistently performs better than the straight path MTLE and tumor ablation in the amygdala and hippocampus. The curved path gave better lesion coverage with a smaller ablation radius and thus has the potential to do less damage to the surrounding tissue.

Software Related Disclosure

Figure 9A:
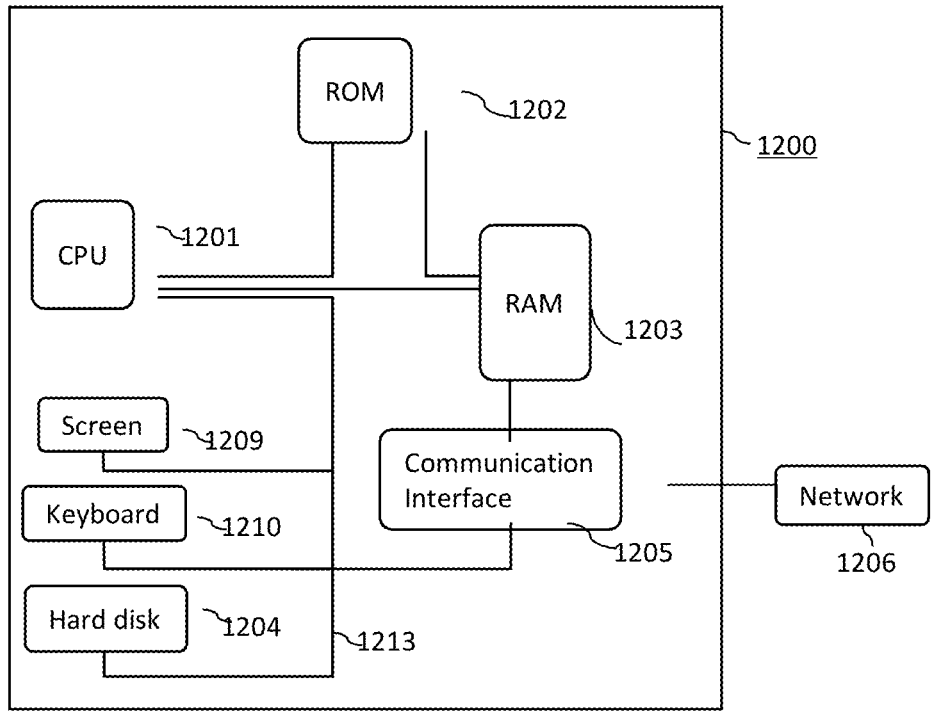
FIG. 9(A) shows a schematic diagram of an embodiment of a computer that may be used with one or more embodiments of at least one apparatus, system, method and/or storage medium of the invention.

Various components of a computer system 1200 are provided in FIG. 9(A). A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 9). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more components or a device or system using same, such as, but not limited to, the system 100, the system 100', the system 100" and/or the system 100''', discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with the software, planning system, and bendable catheter subsystems discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

Figure 9B:
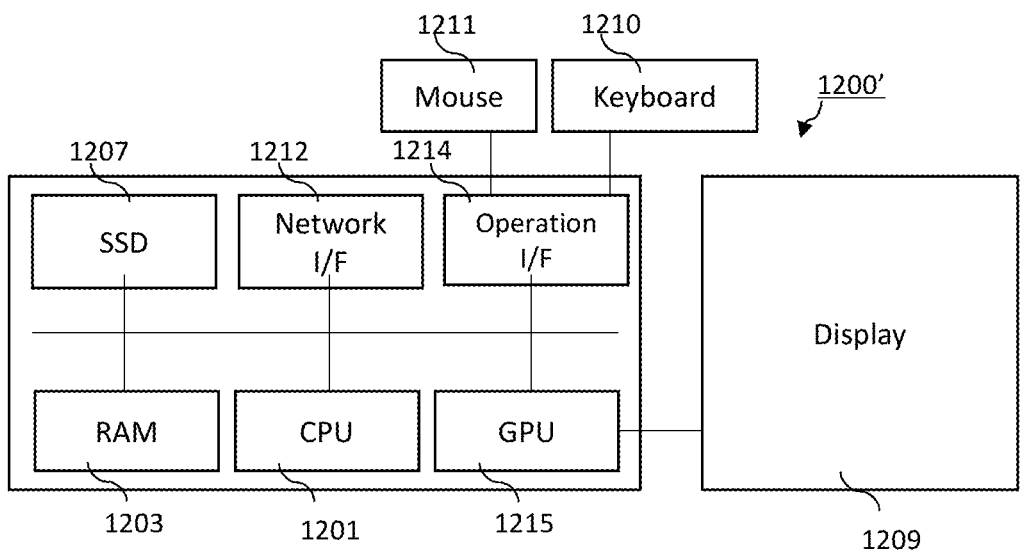
FIG. 9(B) shows a schematic diagram of another embodiment of a computer that may be used with one or more embodiments of at least one apparatus, system, method and/or storage medium of the invention, in accordance with one or more aspects of the present disclosure.

The I/O or communication interface 1205 provides communication interfaces to input and output devices, which may include imaging systems or imaging databases for, for example, MRI imaging systems, a communication cable and a network (either wired or wireless), a keyboard 1210, a mouse (see e.g., the mouse 1211 as shown in FIG. 9(B)), a touch screen or screen 1209, a light pen and so on. The Monitor interface or screen 1209 provides communication interfaces thereto.

Any methods and/or data of the present disclosure, such as the methods for planning, using and/or manufacturing a device, system or storage medium for use with same and/or method(s) for the planning systems, software, and control of the bendable catheter subsystems, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 9(B)), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 9(A). Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 9(A) or 10(B)) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 9(B). The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with one or more other components of a system (e.g., the system 100, the system 100', the system 100", the system 100''', etc.) via the operation interface 1214 or the network interface 1212. For example, the computer 1200' may connect to one or more actuators that control the movement of the bendable catheter subsystem. The operation interface 1214 is connected with an operation unit such as a mouse device 1211, a keyboard 1210, and a controller for the bendable catheter subsystem and/or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the imaging system, the planning system, and the bendable catheter subsystem as well as one or more other components of a system, such as the system 100, 100', 100",100''', etc., to perform the planning and/or interventional therapy. The monitor or display 1209 displays the reconstructed image, and may display other information about the imaging condition or about an object to be imaged. There is also provided a user interface for a user to operate a system (e.g., the system 100, the system 100', the system 100", the system 100''', etc.) as well as to navigate and optionally modify, for example, the entry point, the target volume, or modify the preliminary curved trajectory during planning or implementation. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', etc.).

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated go degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The term "substantially" is intended to allow for deviations from the descriptor that do not negatively affect the intended purpose. For example, deviations that are from limitations in the ability of a clinician to follow a planned pathway as well as, differences within manufacture tolerance. Variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A planning and visualization method comprising:
   acquiring a position of an entry point and a target volume in a medical image;
   defining a preliminary curved path between the entry point and the target volume based on a geometric element of the target volume, wherein the preliminary curved path comprises at least two segments, wherein at least one of the at least two segments is an arc segment;
   modifying the preliminary curved path based on a user input to form a surgical curved path;
   wherein at least one of the preliminary curved path and the surgical curved path is constrained by a physical parameter of a surgical robot and comprises one or more arc segment(s) and at least one straight segment that is concatenated between the one or more arc segment and the entry point; and
   displaying the constrained preliminary curved path or the constrained surgical curved path.

2. The method of claim 1, wherein at least one of the preliminary curved path and the surgical curved path comprises two or more concatenated arc segments and at least one straight segment.

3. The method of claim 1, wherein the preliminary curved path and the surgical curved path are constrained by the physical parameters of the surgical robot.

4. The method of claim 1, wherein the preliminary curved path is based on the centerline of the target volume.

5. The method of claim 1, wherein modifying the preliminary curved path to form a surgical curved path comprises accepting user input to modify a curvature radius or a bending angle of one or more arc segments.

6. The method of claim 1, further comprising displaying the geometric element to the user as the user modifies the preliminary curved path.

7. The method of claim 1, further comprising displaying the minimum and/or maximum distances from the preliminary curved path or surgical curved path to a boundary of the target volume at a plurality of points along the preliminary curved path or surgical curved path.

8. The method of claim 1, wherein the arc segments are circular arc segments.

9. The method of claim 1, wherein the target volume is a three-dimensional model of an anatomical object that is at least one of a tumor, amygdala, hippocampus, blood vessels, ventricles, optic tracts, optic chiasm, optic nerves, and brain stem.

10. A system for planning and visualizing a curved path comprising:
    a computer implemented planning and visualization subsystem configured to:
    identify an entry point and target volume in a medical image;
    define a preliminary curved path between the entry point and the target volume based on a geometric element of the target volume, wherein the preliminary curved path comprises at least two segments, wherein at least one of the at least two segments is an arc segment, the arc segment being defined in three dimensional space with arc parameters, which include at least two of: an arc length, a curvature radius, a bending angle and a bending plane;
    accept user input to modify the preliminary curved path and form a surgical curved path;
    wherein at least one of the preliminary curved path and the surgical curved path is constrained by a physical parameter of a surgical robot; and
    displaying the constrained preliminary curved path or the constrained surgical curved path.

11. The system of claim 10, wherein the preliminary curved path comprises two or more concatenated arc segments and at least one straight segment.

12. The system of claim 10, wherein the constrained preliminary curved path and the target volume are displayed superimposed with the medical image.

13. The system of claim 10, wherein the target volume is a three-dimensional model of an anatomical object that is at least one of a tumor, amygdala, hippocampus, blood vessels, ventricles, optic tracts, optic chiasm, optic nerves, brain sulci and brain stem.

14. The system of claim 10, further comprising a user interface configured to input user information for the identification of the entry point and the target volume and the modification of the preliminary curved path.

15. The system of claim 10, wherein the planning and visualization subsystem is configured to revise at least one of the entry point, the target volume, and the preliminary curved path based on user input through the user interface.

16. A medical planning and implementation system comprising;
    a computer implemented planning and visualization subsystem configured to perform the method of claim 1, and
    a surgical robot comprising at least a first bending section and a second bending section,
    wherein the preliminary curved path comprises at least a first arc segment and a second arc segment and an arc lengths of the first arc segments corresponds to the first bending section and an arc length of the second arc segment corresponds to a length of the second bending section.

17. The medical planning and implementation system of claim 16, wherein the preliminary curved path or surgical curved path comprises two or more concatenated arc segments and at least one straight segment proximal to the two or more arc segments and the surgical robot further comprises at least one straight proximal section.

18. The medical planning and implementation system of claim 16, wherein the preliminary curved path or surgical curved path and the target volume are displayed superimposed with the medical image.

19. A method of treating a patient having temporal lobe epilepsy (TLE) comprising:
    acquiring a position of an entry point in a medical image of the patient;
    defining a preliminary curved path between the entry point and a geometric element of the amygdala and hippocampus, wherein the preliminary curved path comprises at least two segments, wherein at least one of the at least two segments is an arc segment;
    modifying the preliminary curved path based on a user input to form a surgical curved path;
    wherein at least one of the preliminary curved path and the surgical curved path is constrained by a physical parameter of a surgical robot;
    displaying the constrained preliminary curved path or the constrained surgical curved path; and
    providing laser interstitial thermal therapy (LITT) to the patient using a surgical robot comprising two or more bending sections, the LITT provided substantially along the surgical curved path.

20. The method of claim 1, further comprising displaying the target volume.

21. The method of claim 2, wherein the two or more concatenated arc segments are each defined in three dimensional space with arc parameters, which include at least two of: an arc length, a curvature radius, a bending angle and a bending plane.

* * * * *